United States Patent
Dasai et al.

(10) Patent No.: US 9,976,981 B2
(45) Date of Patent: May 22, 2018

(54) DEVICE FOR DETECTING CHEMICAL/PHYSICAL PHENOMENON HAVING A DIFFUSION LAYER FORMED BETWEEN AN INPUT CHARGE CONTROL REGION AND A SENSING REGION ON A SUBSTRATE

(71) Applicant: National University Corporation Toyohashi University of Technology, Toyohashi-shi, Aichi (JP)

(72) Inventors: Fumihiro Dasai, Toyohashi (JP); Kazuaki Sawada, Toyohashi (JP)

(73) Assignee: National University Corporation Toyohashi University of Technology, Aichi (JP)

( * ) Notice: Subject to any disclaimer, the term of this patent is extended or adjusted under 35 U.S.C. 154(b) by 0 days. days.

(21) Appl. No.: 15/543,169

(22) PCT Filed: Jan. 6, 2016

(86) PCT No.: PCT/JP2016/050276
§ 371 (c)(1),
(2) Date: Jul. 12, 2017

(87) PCT Pub. No.: WO2016/114202
PCT Pub. Date: Jul. 21, 2016

(65) Prior Publication Data
US 2018/0003671 A1 Jan. 4, 2018

(30) Foreign Application Priority Data
Jan. 14, 2015 (JP) .................................. 2015-005400

(51) Int. Cl.
*H01L 29/762* (2006.01)
*G01N 27/414* (2006.01)
*B82Y 30/00* (2011.01)

(52) U.S. Cl.
CPC ............ *G01N 27/414* (2013.01); *B82Y 30/00* (2013.01)

(58) Field of Classification Search
CPC .... H01L 29/762; G11C 19/285; G01N 27/60; G01N 27/4148; G01N 27/414
See application file for complete search history.

(56) References Cited

U.S. PATENT DOCUMENTS 5,247,554 A * 9/1993 Yamada ............... G11C 19/285
257/239
6,255,678 B1 * 7/2001 Sawada .................... G01K 1/02
257/252

(Continued)

FOREIGN PATENT DOCUMENTS

JP H06-268191 A 9/1994
JP 4171820 B2 8/2008

(Continued)

OTHER PUBLICATIONS

International Search Report for PCT/JP2016/050276, with translation, dated Jul. 18, 2017.

*Primary Examiner* — Andrew Q Tran
(74) *Attorney, Agent, or Firm* — Gavin J. Milczarek-Desai; Quarles & Brady LLP

(57) ABSTRACT

Provided is a charge-transfer-type sensor suitable for high integration while eliminating a potential barrier. A sensor provided with a semiconductor substrate 10 partitioned into a sensing region 5 in which a potential varies in corresponding fashion to a variation in the external environment, a charge input region 2 for supplying charges to the sensing region 5, an input charge control region 3 interposed between the sensing region 5 and the charge input region 2, and a charge accumulation region 7 for accumulating electric charges transported from the sensing region 5, the sensor for detecting the amount of electric charges accumulated in (Continued)

the charge accumulation region 7, wherein a diffusion layer 4 is formed between the input charge control region 3 and the sensing region 5 of the substrate 10, and dopants for producing charges having the same polarity as the charges supplied from the charge input region 2 are diffused in the diffusion layer 4.

3 Claims, 4 Drawing Sheets

(56) References Cited

U.S. PATENT DOCUMENTS

| | | |
|---|---|---|
| 7,826,980 B2 | 11/2010 | Sawada et al. |
| 2008/0231253 A1 | 9/2008 | Sawada et al. |
| 2010/0052080 A1 | 3/2010 | Garcia Tello et al. |

FOREIGN PATENT DOCUMENTS

| | | |
|---|---|---|
| JP | 2008-209143 A | 9/2008 |
| JP | 2010-122090 A | 6/2010 |
| JP | 2010-52360 A | 7/2010 |
| JP | 2013-174602 A | 9/2013 |

\* cited by examiner

DEVICE FOR DETECTING CHEMICAL/PHYSICAL PHENOMENON HAVING A DIFFUSION LAYER FORMED BETWEEN AN INPUT CHARGE CONTROL REGION AND A SENSING REGION ON A SUBSTRATE

TECHNICAL FIELD

The present invention relates to an improvement of a chemical/physical phenomenon detecting device.

BACKGROUND ART

As a chemical/physical phenomenon detecting device, a cumulative chemical/physical phenomenon detecting device disclosed in Patent Document 1 is known.

This detection device is used as, for example, a pH sensor, and removes the influence of remaining charges due to a potential barrier (so-called "bump" of potential). The remaining charges can be a factor in generating a false signal so that the charges should be removed to perform high-sensitivity detection.

In a prior chemical/physical phenomenon detection device, this potential barrier is formed at a position adjacent to the first charge control electrode which defines the potential of an Input Charge Control (ICG) region. That is, a silicon nitride film defining the sensing region on the substrate inherently covers the first charge control electrode according to the manufacturing process of the device, so that the silicon nitride film becomes thick on the side surface of the first charge control electrode. Hence, the external environment is not sufficiently reflected in the potential change of the substrate.

As a method for removing the influence of the remaining charges due to the potential barrier, a charge removal well is provided between the input charge control region and the sensing region. By controlling the potential of this removal well, the remaining charges in the sensing region are forcedly attracted to this removal well, thereby preventing the generation of the false signal.

PRIOR ART DOCUMENT

Patent Document

Patent Document 1: Japanese Patent No. 4171820
Patent Document 2: Published Japanese Translation No. 2010-525360

SUMMARY OF THE INVENTION

Problems to be Solved by the Present Invention

A second charge control electrode is disposed at a position corresponding to the removal well in addition to the first charge control electrode for controlling the potential of the removal well formed between the sensing region and the input charge control region.

On the other hand, techniques for two-dimensionally measuring changes in the external environment such as pH by integrating the chemical/physical phenomena detection devices are being developed, and in this development, a higher density of integration of the devices is required.

A chemical/physical phenomenon detection device disclosed in Patent Document 1 adopting a structure in which a second charge control electrode and a wiring for driving the second charge control electrode are added is not preferable from the viewpoint of high integration thereof.

Of course, it is needless to say that a higher sensitivity is required for a chemical/physical phenomenon detection device, so the influence of the false signal caused by the potential barrier must be eliminated.

In view of the above, it is an object of the present invention to provide a chemical/physical phenomenon detecting device suitable for high integration while eliminating a potential barrier.

Means to Solve the Problems

As a result of intensive studies to achieve such object, the present inventors have conceived the chemical/physical phenomenon detecting device of the first aspect. That is, A chemical/physical phenomenon detection device comprising;

a sensing region in which the potential of the sensing region changes in accordance with a change in an external environment, a charge input region for supplying charges to the sensing region, an input charge control region interposed between the sensing region and the charge input region, and a charge accumulation region for accumulating charges transferred from the sensing region, wherein a diffusion layer is formed between the input charge control region and the sensing region on a substrate, and dopants for generating charges having the same polarity as that of the charges supplied from the charge input region are diffused in the diffusion layer.

According to the chemical/physical phenomenon detecting device of the first aspect defined as above, in the diffusion layer formed between the input charge control region and the sensing region, the potential in a neutral state of the diffusion layer is supplied from the potential of the sensing region. Here, the neutral state means a state in which no charge is present in the diffusion layer, and in this state, the potential of the sensing region is different from the potential of the diffusion layer. That is, when electrons are adopted as the charges to be input, the potential of the diffusion layer is always higher than the potential of the sensing region. As a result of the doped diffusion layer, no potential barrier is formed between the charge supply control region and the sensing region.

According to the chemical/physical phenomenon detecting device defined in the first aspect, the electrode for controlling the potential of the charge removal well and wiring therefor are not required so that it is suitable for the requirement of high density integration in comparison with the conventional chemical/physical phenomena detecting device in which a charge removal well is formed to remove the potential barrier.

In the chemical/physical phenomenon detection device defined in the first aspect, the charge input (ID) region is also doped to be the same semiconductor type as the diffusion layer. For example, when the charges supplied from the charge input region are electrons, the charge input region and the diffusion layer are doped n-type to the semiconductor substrate. Therefore, in order to simplify the manufacturing process of the chemical/physical phenomenon detection device, it is preferable to dope the charge input region, the diffusion layer, and the charge accumulation region also using the same mask.

As a result, the chemistry/physical phenomenon detection device according to the second aspect of the present invention is defined as follows.

The chemical/physical phenomenon detection device according to claim 1, wherein the same dopant is diffused into the diffusion layer and the charge input region.

DETAILED DESCRIPTION OF THE INVENTION

First Embodiment

Figure 1:
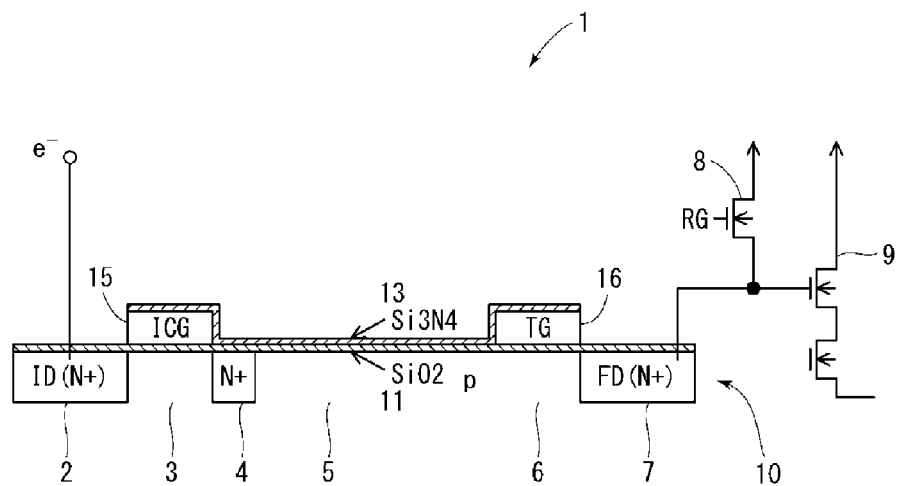
FIG. 1 is a cross-sectional view showing a configuration of a pH sensor according to a first embodiment of the present invention.

FIG. 1 shows the principle configuration of the chemical/physical phenomenon detection device 1 according to the first embodiment of the present invention.

The chemical/physical phenomenon detection device 1 is comprised of a silicon substrate 10 and a structure stacked on the silicon substrate 10.

Figure 3:
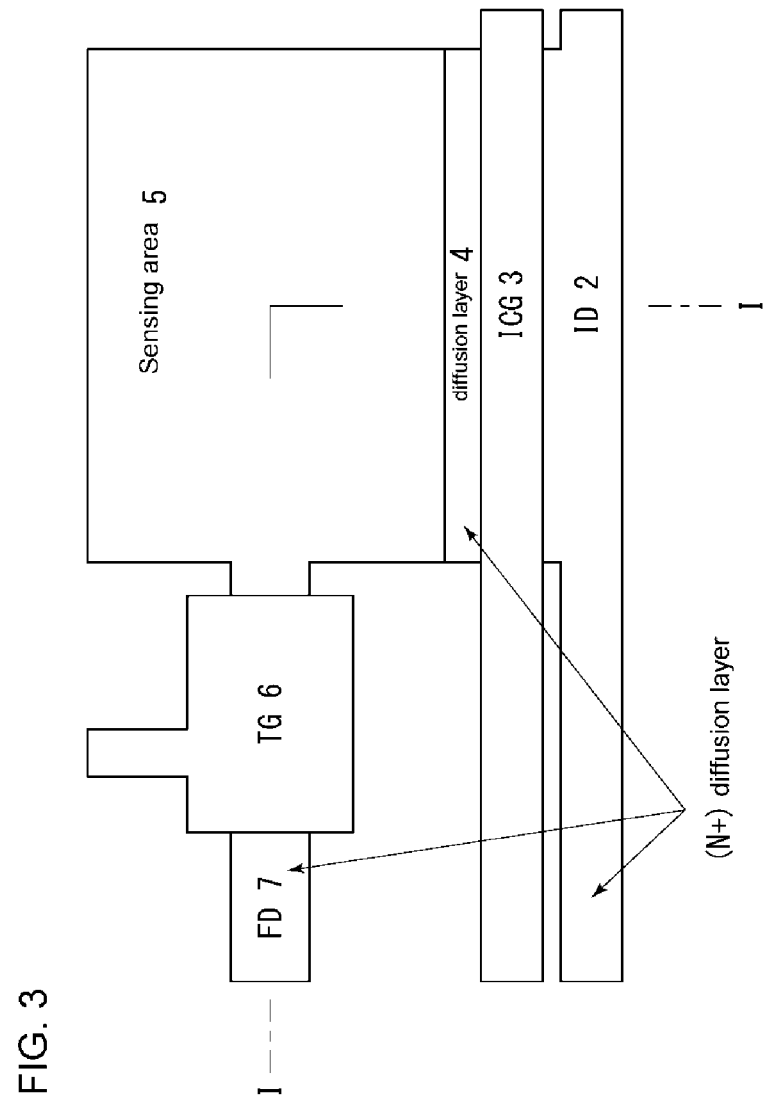
FIG. 3 shows a planar structure of a pH sensor as well.

On the silicon substrate 10, a charge input (ID) region 2 from which charges are input or supplied, an input charge control (ICG) region 3, a diffusion layer 4, a sensing region 5, a charge transfer control (TG) region 6, and a charge accumulation (FD) region 7 are partitioned in series. In the example of FIG. 3, a rectangular sensing region is adopted and a diffusion layer 4—input charge control region 3—charge input region 2 are formed in order from a side of the sensing region as well as the charge transfer control region 6 and the charge accumulation region 7 are formed in order from another side of the sensing region 5. All of regions can be aligned linearly. The section of each region is defined by the difference in semiconductor type on the surface of the semiconductor substrate 10. For example, when electrons are used as charges, the charge input (ID) region 2, the diffusion layer 4 and the charge accumulation (FD) region 7 are n+ type regions, and the input charge control (ICG) region 3 and the sensing region 5 are p-type regions.

In the charge accumulation region 7, a reset unit 8 for discharging the charges accumulated in the charge accumulation region 7 and a charge amount detection unit 9 for detecting an amount of charges in the charge accumulation region. A well-known conventional circuit is adopted for the reset unit 8 and the charge amount detection unit 9.

A silicon oxide insulating layer 11 is stacked on the surface of the substrate 10, and on the layer 11, an ICG electrode 15 is mounted at a position opposed to the input charge control region 3 and the potential of the input charge control region 3 is controlled by the ICG electrode 15. A TG electrode 16 for controlling the potential of the charge transfer control region 6 is formed as well at a position opposed to the region 6. In a portion corresponding to the sensing region 5, a silicon nitride layer 13 is stacked as a sensitive layer. Since the silicon nitride layer 13 is formed after the ICG electrode 15 and the TG electrode 16, the silicon nitride layer 13 also covers these electrodes.

An area and planar shape of each region, the amount of dopant introduced, and the material of the sensitive film can be arbitrarily designed in consideration of the object to be measured, measurement conditions, required sensitivity and the like.

Both the charge input region 2, the diffusion layer 4, and the charge accumulation region 7 are doped with an n-type dopant. Before forming the insulating layer 11, the doping is performed by masking the surface of the substrate 10 and implanting an n-type dopant. From the viewpoint of minimizing the number of times of mask processing, it is preferable to make the doping conditions be the same for the charge input region 2, the diffusion layer 4, and the charge accumulation region 7. As a result, the same dopant is introduced into these three regions at the same concentration by one doping treatment.

According to the chemical/physical phenomenon detecting device 1 shown in FIG. 1, even if the silicon nitride layer 13 exists on the side surface of the ICG electrode 15, the region of the substrate opposed thereto exists as the diffusion layer 4. Since the dopant for increasing the potential of the diffusion layer 4 is diffused therein, the formation of the potential barrier is prevented.

Figure 2:
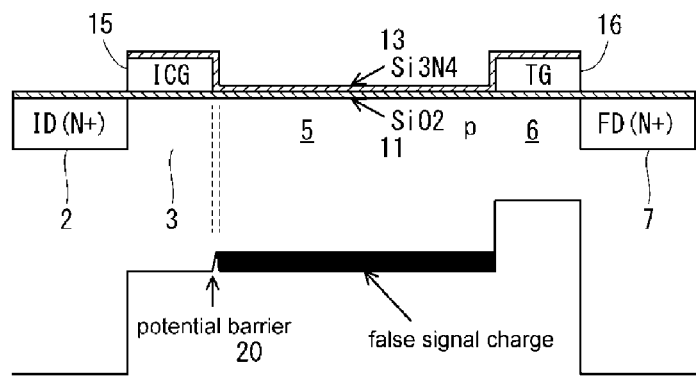
FIG. 2 is a schematic diagram showing a potential barrier formed when the diffusion layer is omitted from the pH sensor of the first embodiment.

FIG. 2 shows the potential of each region when the diffusion layer 4 is omitted. In FIG. 2, reference numeral 20 denotes a potential barrier. In the example of FIG. 1, since the diffusion layer 4 having a potential higher than that of the sensing region 5 is formed at the position where the potential barrier 20 is formed, the potential barrier 20 is buried therein and disappears.

When holes are used as charges, the diffusion layer 4 has a potential lower than that of the sensing region 5. In other words, the potential of the diffusion layer 4 is far from the potential of the sensing region 5 when viewed from the neutral state of the diffusion layer 4.

As to the diffusion layer 4, when the silicon nitride layer 13 covering the side surface of the ICG electrode 15 on the side of the sensing region 5 is projected onto the diffusion layer 4 below in FIG. 1, the projected silicon nitride layer 13 is contained in the diffusion layer 4.

FIG. 3 shows the plan structure of the chemical/physical phenomenon detection device 1. As shown in FIG. 3, the diffusion layer 4 is formed between the ICG region 3 and the sensing region 5. Note that FIG. 1 is a cross-sectional structure taken along line I-I in FIG. 3.

The width of the diffusion layer 4 can be arbitrarily set in consideration of etching conversion difference and mask shift. In this embodiment, the width of the diffusion layer 4 is set to 1.20 μm in the 2.0 μm process (that is, the minimum channel length is 2.0 μm).

Next, the operation of the chemical/physical phenomenon detection device 1 will be described with reference to FIG. 4.

FIG. 4(a) shows a reset step. In this reset step, the reset gate RG of the reset unit 8 is at a high potential, and the charges in the charge accumulation (FD) region (hereinafter may be simply referred to as "FD region") 7 are discharged to the outside of the device.

FIG. 4(b) shows a standby step. In this standby step, the reset gate RG of the reset section 8 becomes a low potential, so that charges can be accumulated in the FD region 7.

FIGS. 4(c) and (d) show the measurement step. As a premise of this step, the potential of the sensing region 5 varies depending on the external environment (the pH of the measurement object). First, as shown in FIG. 4(c), charges (in this case, electrons) are injected from the charge input (ID) region (hereinafter sometimes simply referred to as "ID region") 2 and then charges go over an input charge control (hereinafter simply referred to "ICG region") 3 and arrive or get into the sensing region 5. After that, as shown in FIG. 4(d), when the charge supply from the ID region 2 is stopped, charges above the sensing region 5 are leveled by the ICG region 3. At this time, the potential deference between the ICG region 3 and the sensing region 5 depends on the pH of the object to be measured, and an amount of charge corresponding to the potential difference remains on the sensing region 5.

Since the potential of the diffusion layer 4 is set to be sufficiently higher than the potential of the sensing region 5, no potential barrier is formed between the ICG region 3 and the sensing region 5.

In the measurement step shown in FIG. 4(d), charges also exist in the diffusion layer 4, and the input charges remain on the layer 4. An amount of charges, including the remaining charges on the diffusion layer, depending on the potential difference between the ICG region 3 and the sensing region 5 defines the pH value of the object to be measured. In other words, the charges existing in the charge well due to the diffusion layer 4 has no influence on the amount of charges that can define the pH value.

FIGS. 4(e) and 4(f) show the charge transfer step. The potential of the charge transfer control (TG) region 6 is raised and the charges remaining in the step of FIG. 4(d) are transferred to and in the charge accumulation (FD) region 7. Hereinafter the charge transfer (TG) region may be simply referred as TG region, and the charge accumulation (FD) region may be simply referred as FD region.

By repeating the steps in FIGS. 4(c) to 4(f), a small change in pH can be converted to a large change in charge amount.

In FIG. 4(g), the amount of charges in the FD region 7 is converted to an electric signal by the charge detection section 9. This makes it possible to specify the pH value.

Hereinafter, the steps of FIG. 4(a) to FIG. 4(g) are repeated.

Figure 5:
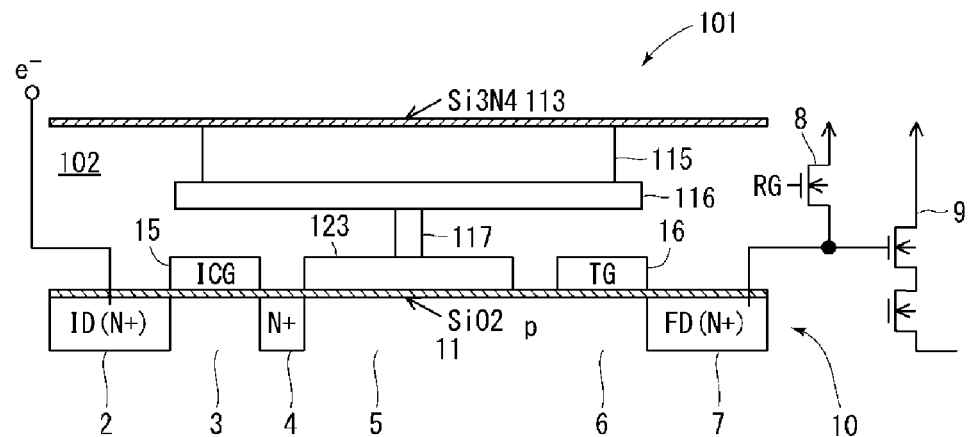
FIG. 5 is a cross-sectional view showing a configuration of a pH sensor according to a second embodiment of the present invention.

FIG. 5 shows an extended type chemical/physical phenomenon detecting device 101. The same elements as those in FIG. 1 are denoted by the same reference numerals, and a description thereof will be partially omitted.

The chemical/physical phenomenon detection device 1 of the direct type in FIG. 1 and the chemical/physical phenomenon detection device 101 in FIG. 5 adopt the same configuration in the substrate 10, and they are different in structure with regard to stacked layers formed on the silicon oxide insulating layer 11 on the substrate.

In the chemical/physical phenomenon detecting device 101 shown in FIG. 5, a silicon oxide layer 102 is stacked on the entire surface of the insulating layer 11, and a silicon nitride layer 113 as a sensitive layer is stacked on the surface of the silicon oxide layer 102. The potential change of the silicon nitride layer 113 is transmitted to the sensing region defining electrode 123 via the conductive layers 115, 116, and 117 made of a metal material or the like buried in the silicon oxide layer 102.

As a result, the potential of the silicon nitride layer 113 corresponding to the pH of the measurement object is reflected on the potential of the sensing region 5.

It is to be noted that the extended type chemical/physical phenomenon detecting device 101 shown in FIG. 5 can be made by a conventional process and, of course, the silicon oxide layer can be formed in multiple layers (see Published Japanese Translation No. 2010-535360, (he description of this literature is incorporated as part of this specification by reference).

Figure 6:
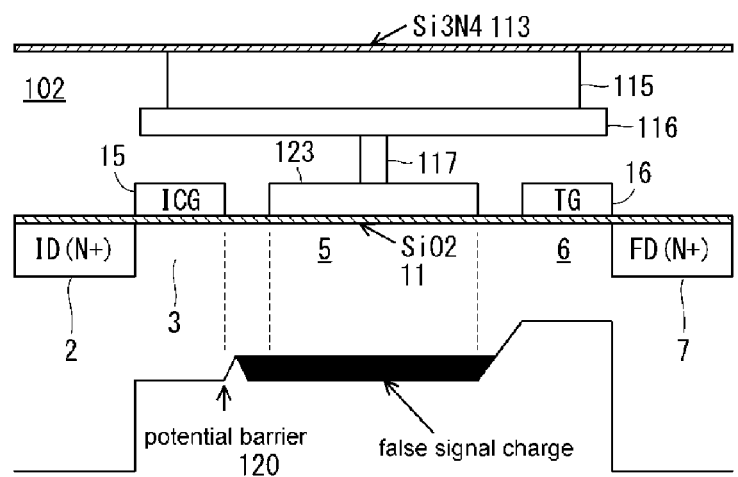
FIG. 6 is a schematic diagram showing a potential barrier formed when the diffusion layer is omitted from the pH sensor of the second embodiment.

Even with the chemical/physical phenomenon detecting device 101 shown in FIG. 5, unless the diffusion layer 4 is formed between the ICG region 3 and the sensing region 5 in the substrate 10, as shown in FIG. 6, the potential barrier 120 is formed to retain the charges on the sensing region and the charges thus retained may cause a false signal.

On the other hand, as shown in FIG. 5, by forming the diffusion layer 4 between the ICG layer 3 and the sensing region 5, the potential barrier 120 is not formed.

Figure 4:
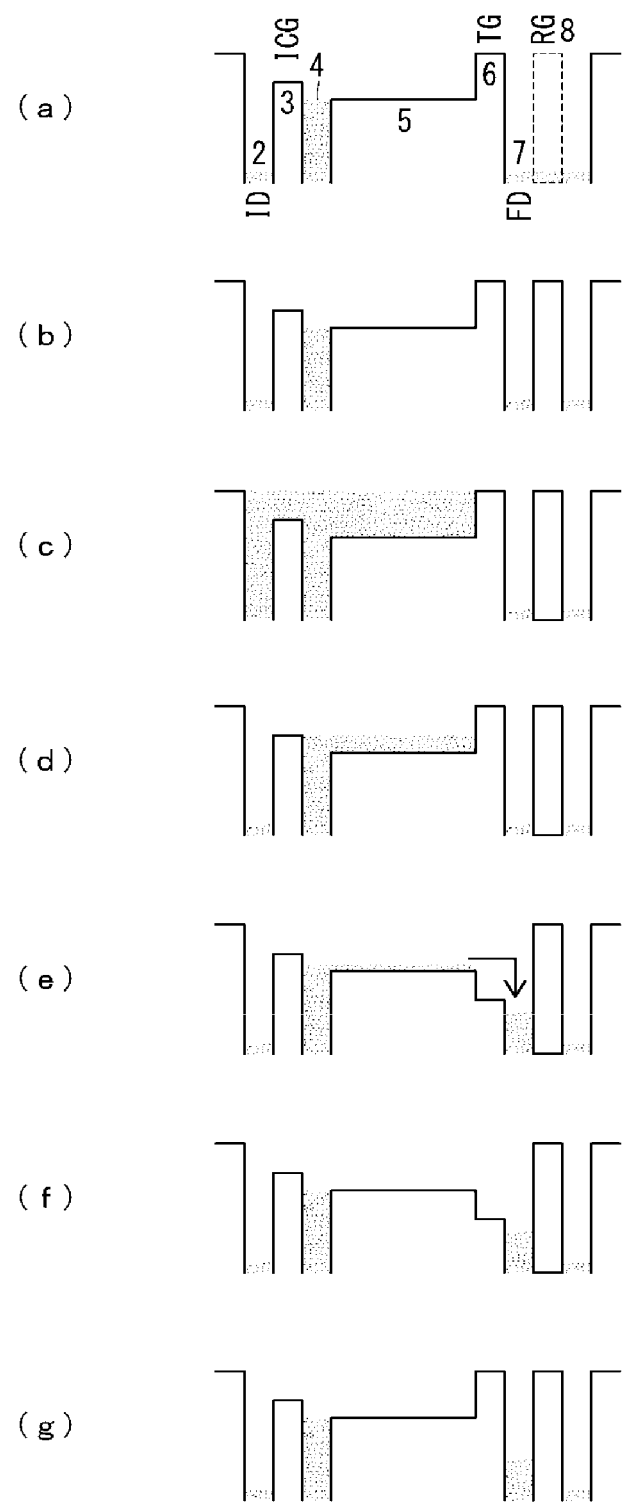
FIG. 4 shows the operation of the pH sensor of the first embodiment.

The chemical/physical phenomenon detecting device 101 also operates in the same manner as the chemistry/physical phenomenon detecting device in FIG. 1 (see FIG. 4).

The present invention is not limited to the description of the embodiment and examples of the invention at all. Various modifications are also included in the present invention as long as they can be easily conceived by those skilled in the art without departing from the spirit of the scope of claims.

EXPLANATION OF NUMERAL NUMBERS IN FIGS 1 101 chemical/physical phenomena detection device
2 charge input (ID) region
3 input charge control (ICG) region
4 diffusion layer
5 sensing region
6 charge transfer control (TG) region
7 charge accumulation (FD) region
8 reset unit
9 charge amount detection unit
10 substrate
15 ICG electrode
16 TG electrode
115, 116, 117 conductive layer
123 sensing region defining electrode

The invention claimed is:
1. A chemical/physical phenomenon detection device comprising;
   a sensing region in which potential of the sensing region changes in accordance with a change in an external environment,
   a charge input region for supplying charges to the sensing region,
   an input charge control region interposed between the sensing region and the charge input region, and
   a charge accumulation region for accumulating the charges transferred from the sensing region,
   wherein a diffusion layer is formed between the input charge control region and the sensing region on a substrate, and a dopant is diffused into the diffusion layer for donating charges having the same polarity as the charges supplied from the charge input region.
2. A device according to claim 1, wherein the same dopants are diffused in the diffusion region and the input charge control region.
3. A device according to claim 1, wherein the charges from the charge input region are electrons.

* * * * *